US011911080B2

(12) United States Patent
George

(10) Patent No.: US 11,911,080 B2
(45) Date of Patent: *Feb. 27, 2024

(54) ROD REDUCING APPARATUS AND ASSOCIATED METHODS

(71) Applicant: GLOBUS MEDICAL, INC., Audubon, PA (US)

(72) Inventor: Milan George, Collegeville, PA (US)

(73) Assignee: Globus Medical, Inc., Audubon, PA (US)

( * ) Notice: Subject to any disclaimer, the term of this patent is extended or adjusted under 35 U.S.C. 154(b) by 824 days.

This patent is subject to a terminal disclaimer.

(21) Appl. No.: 16/870,004

(22) Filed: May 8, 2020

(65) Prior Publication Data
US 2020/0261127 A1   Aug. 20, 2020

Related U.S. Application Data

(60) Continuation of application No. 15/668,787, filed on Aug. 4, 2017, now Pat. No. 10,675,066, which is a division of application No. 13/270,469, filed on Oct. 11, 2011, now Pat. No. 9,750,548.

(51) Int. Cl.
A61B 17/70 (2006.01)
A61B 90/00 (2016.01)

(52) U.S. Cl.
CPC ...... A61B 17/7091 (2013.01); A61B 17/7086 (2013.01); A61B 2090/037 (2016.02)

(58) Field of Classification Search
CPC .................. A61B 17/7086; A61B 17/7091
See application file for complete search history.

(56) References Cited

U.S. PATENT DOCUMENTS

| | | | |
|---|---|---|---|
| 6,440,133 B1 | 8/2002 | Beale | |
| 7,608,081 B2 | 10/2009 | Abdelgany | |
| 7,892,258 B2 | 2/2011 | Iott | |
| 8,012,186 B2 | 9/2011 | Pham | |
| 8,216,241 B2* | 7/2012 | Runco | A61B 17/7032 606/104 |
| 8,317,796 B2* | 11/2012 | Stihl | A61B 17/7091 606/279 |
| 8,864,767 B2* | 10/2014 | Blain | A61B 17/7086 606/86 A |
| 9,204,909 B2* | 12/2015 | Rezach | A61B 17/7076 |
| 9,814,498 B2* | 11/2017 | Seelig | A61B 17/7086 |
| 9,907,582 B1* | 3/2018 | Olea | A61B 17/7079 |
| 2005/0149053 A1* | 7/2005 | Varieur | A61B 17/7091 606/104 |

(Continued)

Primary Examiner — Lynnsy M Summitt

(57) ABSTRACT

Embodiments are generally directed to an apparatus for reducing a rod into an orthopedic fixation device. An embodiment provides a rod-reducing apparatus. The rod-reducing apparatus may comprise a housing comprising a threaded through bore. The rod-reducing apparatus further may comprise a reduction shaft comprising a shaft portion and a through bore in the shaft portion, wherein the shaft portion may be configured to be received within the threaded through bore of the housing. The locking cap driver may comprise a locking cap driver comprising a shaft portion that may be configured to be received within the through bore of the reduction shaft, wherein a distal end of the shaft portion may be configured for attachment to a locking cap assembly.

14 Claims, 5 Drawing Sheets

(56) References Cited

U.S. PATENT DOCUMENTS

| | | | | |
|---|---|---|---|---|
| 2008/0015601 | A1* | 1/2008 | Castro | A61B 17/7089 |
| | | | | 606/86 R |
| 2008/0228233 | A1* | 9/2008 | Hoffman | A61B 17/7088 |
| | | | | 606/86 A |
| 2011/0218581 | A1* | 9/2011 | Justis | A61B 17/708 |
| | | | | 606/86 R |
| 2012/0191144 | A1* | 7/2012 | Peultier | A61B 17/7086 |
| | | | | 606/279 |
| 2013/0066385 | A1* | 3/2013 | Benoist | A61B 17/7086 |
| | | | | 606/86 A |
| 2014/0364912 | A1* | 12/2014 | May | A61B 17/7002 |
| | | | | 606/253 |
| 2016/0045227 | A1* | 2/2016 | Stad | A61B 17/7049 |
| | | | | 606/279 |

* cited by examiner

ROD REDUCING APPARATUS AND ASSOCIATED METHODS

CROSS REFERENCE TO RELATED APPLICATIONS

The present application is a continuation of U.S. patent application Ser. No. 15/668,787 filed on Aug. 4, 2017 (published as U.S. Pat. Pub. No. 2017-0325856), which is a divisional application of U.S. patent application Ser. No. 13/270,469 filed on Oct. 11, 2011 (now U.S. Pat. No. 9,750,548), the entire disclosure of each of which is incorporated herein by reference for all purposes.

FIELD OF THE INVENTION

The present invention relates to medical devices, and, in one or more embodiments, to an apparatus for reducing a rod into an orthopedic fixation device.

BACKGROUND OF THE INVENTION

Many types of spinal irregularities can cause pain, limit range of motion, or injure the nervous system within the spinal column. These irregularities can result from, without limitation, trauma, tumor, disc degeneration, and disease. Often, these irregularities are treated by immobilizing a portion of the spine. This treatment typically involves affixing a plurality of fixation devices to one or more vertebrae and connecting the devices to an elongate rod that generally extends in the direction of the axis of the spine. Typically, fixation devices may include a bone fastener (e.g., bone screw, hook, etc.) for coupling the fixation device to vertebra. Fixation devices further may include a head for coupling the bone fastener to the rod. The process of placing the rod within or adjacent to the head so that they can be coupled together is referred to as "reducing" the rod.

Rod reduction is commonly performed by a surgeon using his or her hands and/or rigid tools, such as pliers, levers, or other instrumentation adaptable to create the necessary pushing and/or pulling forces on the implanted fastener and rod. One current technique employs a reduction head attached to the head of the fixation device. The reduction head generally may include tabs that extend from each of the sidewalls of the head of the fixation device, wherein at least a portion of the inner surface of each of tabs is threaded. To reduce the rod into the head of the fixation device, a driving instrument can be threaded through the tabs. One drawback to this technique is that that the instrumentation typically must be higher as the rod needs to be seated at least below 1-2 threads in the channel between the tabs before the driving instrument can be engaged, resulting in larger equipment applying more weight to the implanted fastener. Another drawback to this technique is that, after the rod is reduced, the driving instrument must be unscrewed from the tabs before the tabs can be removed, increasing the time and complexity of the procedure.

Accordingly, there exists a need for new and improved apparatuses for rod reduction.

SUMMARY OF THE INVENTION

An embodiment of the present invention provides a rod-reducing apparatus. The rod-reducing apparatus may comprise a housing comprising a threaded through bore. The rod-reducing apparatus further may comprise a reduction shaft comprising a shaft portion and a through bore in the shaft portion, wherein the shaft portion may be configured to be received within the threaded through bore of the housing. The locking cap driver may comprise a locking cap driver comprising a shaft portion that may be configured to be received within the through bore of the reduction shaft, wherein a distal end of the shaft portion may be configured for attachment to a locking cap assembly.

Further areas of applicability of the present invention will become apparent from the detailed description provided hereinafter. It should be understood that the detailed description and specific examples, while indicating the preferred or exemplary embodiments of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE PREFERRED EMBODIMENTS

Figure 1:
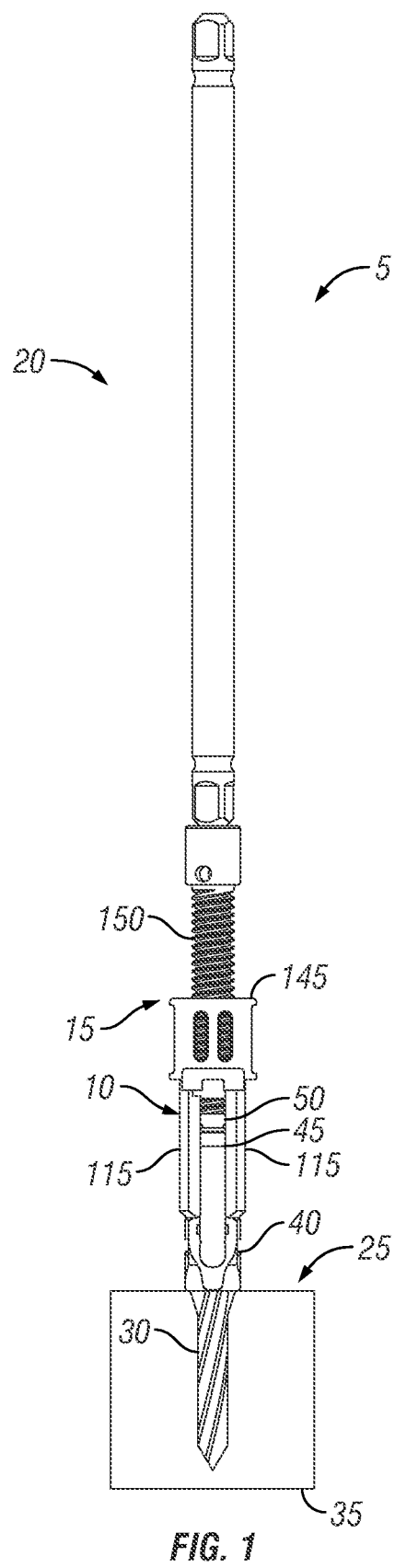
FIG. 1 illustrates a rod-reducing apparatus reducing a rod into an orthopedic fixation device in accordance with embodiments of the present invention.

FIG. 1 illustrates a rod-reducing system 5 in accordance with embodiments of the present invention. In the illustrated embodiment, the rod-reducing system 5 includes a reducing head 10, a rod-reducing apparatus 15, and a driving apparatus 20. Orthopedic fixation device 25 is also shown in the embodiment illustrated by FIG. 1. As illustrated, the orthopedic fixation device 25 may include a bone fastener 30 attached to bone (e.g., vertebral body 35) and a head 40 attached to the bone fastener 30. For positioning of rod 45 into the head 40 of the fixation device 25, the rod-reducing apparatus 15 can be attached to the reducing head 10 which extends from the head 40 in the illustrated embodiment. In accordance with present embodiments, the driving apparatus 20 can then be operated to reduce the rod 45 into the head 40 and engage locking cap assembly 50 with head 40 to secure rod 45 therein.

In one exemplary embodiment, smaller threads are use on the center shaft. This allows for the instrument to be smaller radially. In addition, the smaller threads on the center shaft prevents the splaying of the reduction tabs located on the housing and doesn't need to travel along the length of the reduction tabs. This in turn helps reduce the overall height of the instrument.

Figure 2:
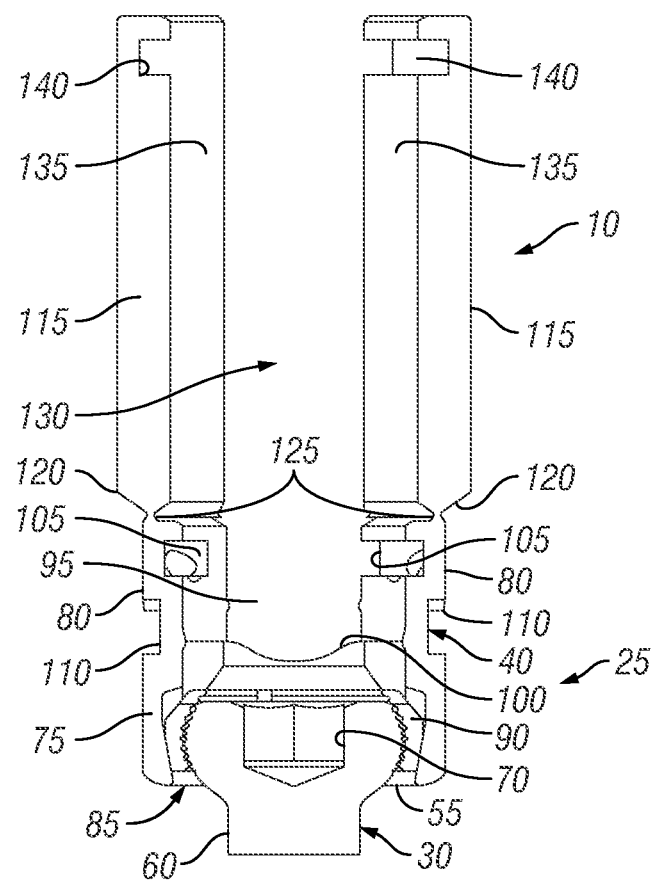
FIG. 2 is a cross-sectional vie of a reducing head coupled to a head of an orthopedic fixation device in accordance with embodiments of the present invention.
Figure 3:
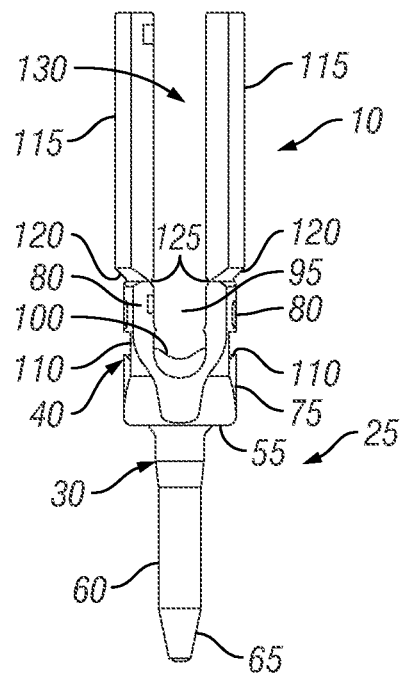
FIG. 3 illustrates a reducing head coupled to a head of an orthopedic fixation device in accordance with embodiments of the present invention.

FIGS. 2 and 3 illustrate the rod-reducing head 10 coupled to the orthopedic fixation device 25 in accordance with embodiments of the present invention. As illustrated, the bone fastener 30 of the orthopedic fixation device 25 may comprise a base portion 55 and an extension, such as shaft 60. The illustrated embodiment shows the shaft 60 having a tapered distal end 65, as best seen in FIG. 3. Those of ordinary skill in the art will appreciate that the shaft 60 may have a number of different features, such as thread pitch, shaft diameter to thread diameter, overall shaft shape, and the like, depending, for example, on the particular application. While the base portion 55 may have any general shape, at least a portion of the base portion 55 may have a curved surface, for example, in order to allow for rotational movement or angular adjustment of the bone fastener 30 with respect to the head 40. In certain embodiments, the base portion 55 may have a tool engagement surface, for example, that can be engaged by a screw-driving tool or other device. The tool engagement surface can permit the physician to apply torsional or axial forces to the bone fastener 30 to drive the bone fastener 30 into the bone (such as vertebral body 35 shown on FIG. 1). In the illustrated embodiment, the tool engagement surface of the base portion 55 is a polygonal recess 70, as best seen in FIG. 2. For instance, the polygonal recess 70 may be a hexagonal recess that receives a hexagonal tool, such as an allen wrench, for example. The present invention is intended to encompass tool engagement surfaces having other shapes, such as slot or cross that may be used, for example, with other types of screwdrivers. In an alternative embodiment (not illustrated), the engagement surface may be configured with a protruding engagement surface that may engage with a tool or device having a corresponding recess.

In the illustrated embodiment, the head 40 of the orthopedic fixation device 25 may comprise a bottom portion 75 and sidewalls 80 that extend upwardly from the bottom portion 75. As illustrated, the bottom portion 75 may have an opening 85 for receiving the base portion 55 of the bone fastener 30. One or more clamping elements 90 may be disposed in the bottom portion 75 for securing the base portion 55 in the head 40, as best seen in FIG. 2. As illustrated, the sidewalls 80 may be generally parallel, for example, and define a recess 95 in the head 40. In accordance with present embodiments, the rod 45 (e.g., FIG. 1) may be reduced into the recess 95. In the illustrated embodiment, a seat 100, which may be U- or wedge-shaped, for example, may be positioned in the head 40 against which the rod 45 may be engaged. The upper portion of the sidewalls 80 may have features, such as slots, recesses, or detents, on an inner surface for engaging the locking cap assembly 50 (e.g., FIG. 1). In the illustrated embodiment, the sidewalls 80 include slots 105 for engaging the locking cap assembly 50, as best seen in FIG. 2. While not illustrated, the locking cap assembly 50 may have corresponding protrusions or slots that permit the locking cap assembly 50 to engage with and rotate with respect to the head 40. The outer portion of the sidewalls 80 may have slots 110, or other suitable features, for receiving an instrument.

While the preceding description of FIGS. 2 and 3 describe a particular embodiment of an orthopedic fixation device 25 to which the reducing head 10 may be attached, it should be understood that the present invention is not limited to any specific configuration for the orthopedic fixation device 25. Rather, the present invention is broad enough to include any of a variety of different devices that can be secured into bone and receive a rod, such as rod 45 (e.g., FIG. 1). For example, the bone fastener 30 may be adapted to have a hook (not illustrated) extending from the base portion 55 rather than the shaft 60, as seen in FIGS. 2 and 3. In an embodiment, the orthopedic fixation device 25 is a pedicle screw.

As illustrated by FIGS. 2 and 3, the reducing head 10 may be coupled to the head 40 of the orthopedic fixation device 25 in accordance with embodiments of the present invention. The reducing head 10 may include, for example, one or more tabs 115 that extend from the sidewalls 80 of the head 40. In the illustrated embodiment, the reducing head 110 includes two tabs 115 with each of the tabs 115 extending from a corresponding one of the sidewalls 80. As illustrated, the distal end 120 of each of the tabs 115 is tapered so that the connection points 125 of the tabs 115 and the sidewalls 80 are a reduced diameter with respect to the tabs 115. This reduced diameter at the connection points 125 should facilitate removal of the tabs 115 from the sidewalls 80 at a desired time. As illustrated, the tabs 115 may generally extend upwardly from the sidewalls 80. Moreover, the tabs 80 may be generally parallel and define a channel 130 for receiving the rod 45 (e.g., FIG. 1). The upper portion of the tabs 115 may have features, such as slots, recesses, or detents, on an inner or outer surface for engaging the rod-reducing apparatus 15. In the illustrated embodiment, the inner surface 135 of the tabs 115 includes slots 140 on the upper portion for engaging the rod-reducing apparatus 15, as best seen in FIG. 2. In some embodiments, the inner surface 135 of the tabs 115 is not threaded.

Figure 4:
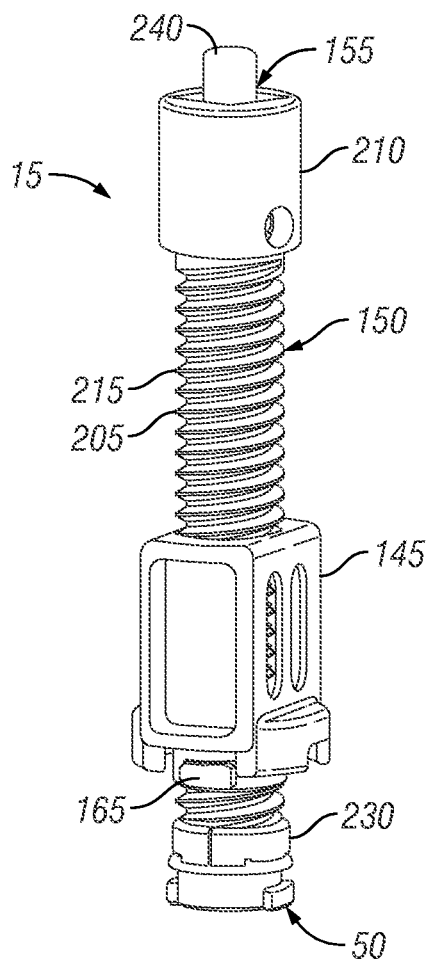
FIG. 4 illustrates a rod-reducing apparatus in accordance with embodiments of the present invention.
Figure 5:
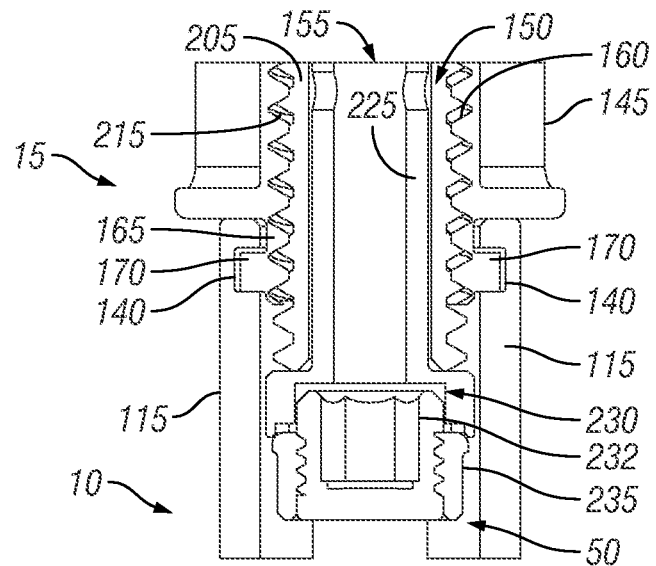
FIG. 5 is a cross-sectional view of a rod-reducing apparatus coupled to a reducing head in accordance with embodiments of the present invention.
Figure 6:
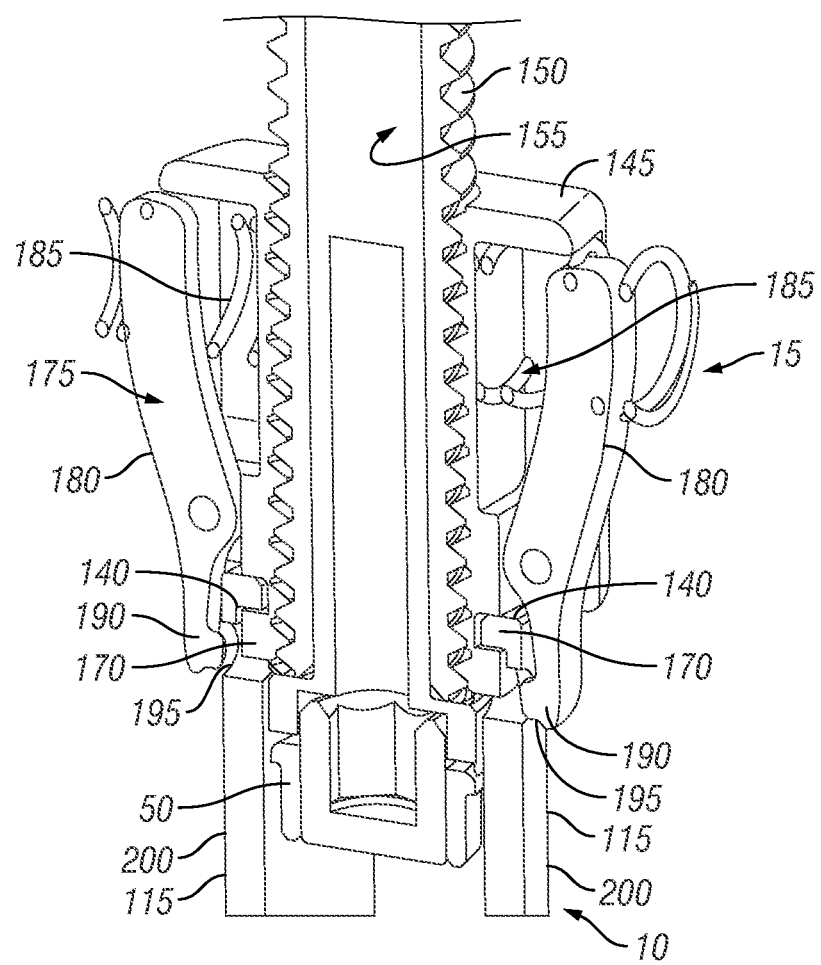
FIG. 6 is a cross-sectional view of a rod-reducing apparatus coupled to a reducing head in accordance with alternative embodiments of the present invention.

FIGS. 4 and 5 illustrate the rod-reducing apparatus 15 in accordance with embodiments of the present invention. As illustrated, the rod-reducing apparatus 15 includes a housing 145, a reduction shaft 150, and a locking cap driver 155. As best seen in FIG. 5, the housing 145 may include a threaded interior surface 150 defining a through bore for receiving the reduction shaft 150. The housing 145 may be configured for attachment to the reducing head 110, for example. In the illustrated embodiment, the housing 145 includes an extension 165 at its distal end. The extension 165 may include one or more features, such as slots or protrusions, for engaging the reducing head 110. As best seen in FIG. 5, the extension 165 may include protrusions 170 that engage corresponding slots 140 in the upper portion of the reducing head 110. It should be understood that other suitable techniques for coupling the housing 145 to the reducing head 110 may also be used in embodiments of the present invention. Referring now to FIG. 6, an alternative technique is illustrated for coupling the housing 145 to the reducing head 110, which may be used in conjunction with, or in place of, the engagement of protrusions 170 with slots 140, in certain embodiments. As illustrated, the housing 145 may include clip-on assembly 175. In the illustrated embodiment, clip-on assembly includes clip-on tabs 180 and clip-on spring 185. The distal end of the clip-on tabs 180 may include one or more features, such as protuberances or recesses, for engaging the reducing head 50. In the illustrated embodiment, the clip-on tabs 180 include protuberances 190 for engaging corresponding recesses 195 in an outer surface 200 of the tabs 115. The spring 185 may be configured to bias the clip-on tabs 180 to secure the housing 145 to the reducing head 10.

Figure 7:
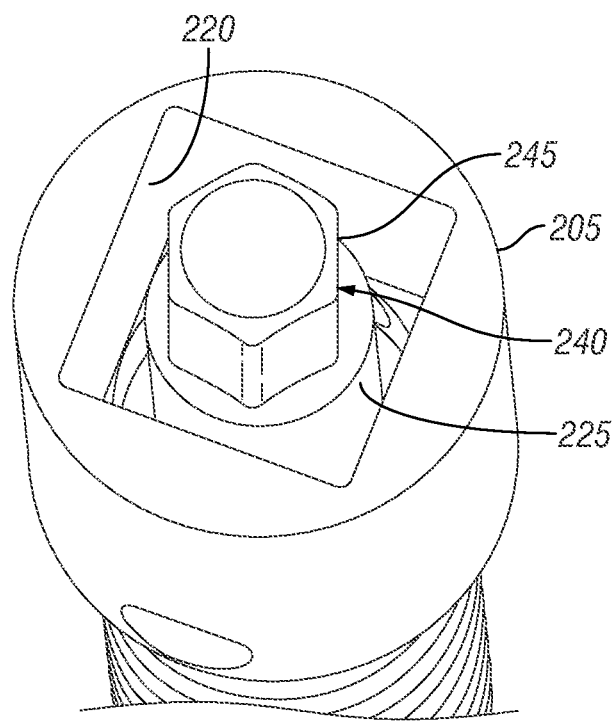
FIG. 7 is a proximal end view of a rod-reducing apparatus in accordance with embodiments of the present invention.

Referring again to FIGS. 4 and 5, the reduction shaft 150 may be threaded into the housing 145 in accordance with embodiments of the present invention. It should be noted that because the reduction shaft 150 is threaded into the housing 145 and not the reducing head 10 (e.g., FIG. 1), the reducing apparatus 15 can be quickly removed from the reducing head 10 after reduction of the rod 45 (e.g., FIG. 1) without the need to unthread the reduction shaft 155. As illustrated, the reduction shaft 150 may include a shaft portion 205 and a connection portion 210. In some embodiments, the shaft portion 205 may be configured and dimensioned to be received within the through bore of the housing 145. As illustrated, at least a portion of the exterior surface of the shaft portion 205 may include threads 215 for engaging the corresponding threaded interior surface 150 of the housing 145. In the illustrated embodiment, the proximal end of the reduction shaft 150 may include the connector portion 210 for connecting the reduction shaft 150 to the driving apparatus 20 (e.g., FIG. 1). As illustrated, the connector portion 210 may have an increased diameter with respect to the shaft portion 205. While the connection portion 210 is illustrated as being generally cylindrical in shape, the geometric configuration of the connection portion 210 is not critical, and the connection portion 210 can have other configurations, such as hexagonal, rectangular, or other suitable geometric configuration. With reference now to FIG. 7, the connection portion 210 may have a tool engagement surface at its proximal end, for example, that can be engaged by the driving apparatus 20 (e.g., FIG. 1). The tool engagement surface can permit the physician to apply torsional or axial forces to the reduction shaft 150 to thread the reduction shaft 150 through the housing 145 (e.g., FIGS. 4 and 5). In the illustrated embodiment, the tool engagement surface of the connector portion 205 is a polygonal recess 220, as best seen in FIG. 7. For instance, the polygonal recess 220 may be a rectangular recess that receives driving apparatus 20 (e.g., FIG. 1). The present invention is intended to encompass tool engagement surfaces having other shapes, such as slot or cross that may be used, for example In an alternative embodiment (not illustrated), the engagement surface may be configured with a protruding engagement surface that may engage with the driving apparatus 20 having a corresponding recess.

As illustrated by FIGS. 4 and 5, the locking cap driver 155 may extend through a through bore in the reduction shaft 150 in accordance with embodiments of the present invention. In some embodiments, the locking cap driver 155 may have a shaft portion 225 that is configured and adapted to be received within the through bore of the reduction shaft 150. In the illustrated embodiment, the distal end of the shaft portion 225 extends beyond the reduction shaft 150 and includes a cap connector portion 230. In some embodiments, the cap connector portion 230 may be configured to engage and retain the locking cap assembly 50. In the illustrated embodiment, the cap connector portion 230 has an opening into which the set screw 232 of the locking cap assembly 50 is received with the set screw 232 threaded into the locking cap 235, as best seen by FIG. 5. As seen in FIG. 5, in certain embodiments, the locking cap 235 does not engage any components of the rod-reducing apparatus 10 as the locking cap assembly 50 is held by the set screw 232. Accordingly, the locking cap 235 should only engage the rod 45 (e.g., FIG. 1) during the reduction process, thus reducing the possibility for any additional stresses/surface indentations during the reduction process, in accordance with embodiments of the present invention. With additional reference to FIG. 7, a driver connection portion 240 may be at the distal end of the shaft portion 225. As best seen in FIG. 7, the driver connection portion 240 may have a tool engagement surface at its proximal end, for example, that can be engaged by the driving apparatus 20 (e.g., FIG. 1). The tool engagement surface can permit the physician to apply torsional or axial forces to the locking cap driver 155, which are then transmitted to the locking cap assembly 50. In the illustrated embodiment, the tool engagement surface of the driver connector portion 240 is a polygonal protrusion 245, as best seen in FIG. 7. For instance, the polygonal protrusion 245 may be a hexagonal protrusion that may engage with the driving apparatus 20 having a corresponding recess. The present invention is intended to encompass tool engagement surfaces having other shapes, such as slot or cross that may be used, for example In an alternative embodiment (not illustrated), the engagement surface may be configured with a recess that may engage with the driving apparatus 20 having a corresponding protrusion.

Figure 8:
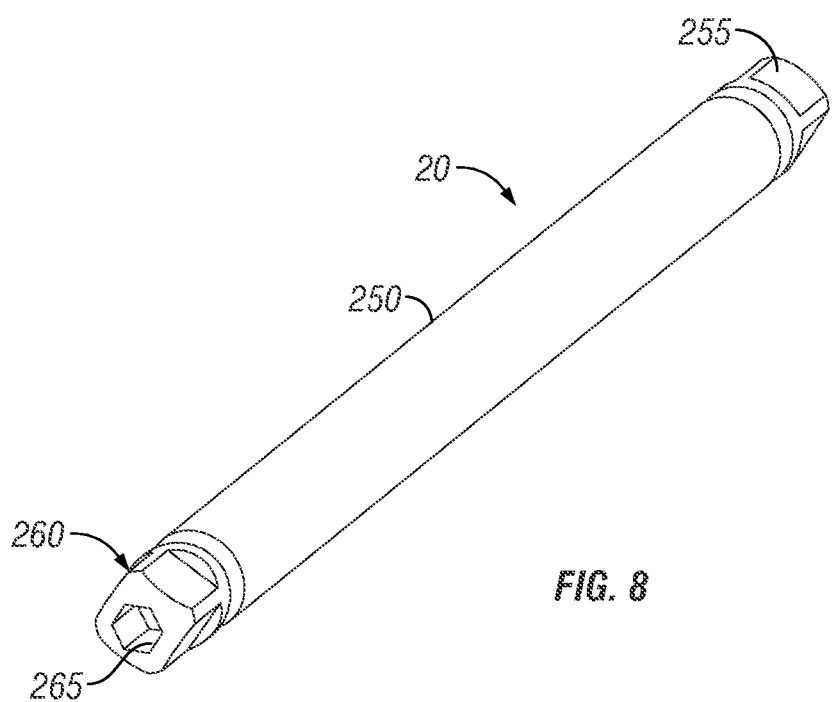
FIG. 8 illustrates a driving apparatus in accordance with embodiments of the present invention.

FIG. 8 illustrates the driving apparatus 20 in accordance with embodiments of the present invention. As illustrated, the driving apparatus 20 includes an elongate shaft portion 250, a reduction shaft engagement portion 255 at one end of the shaft portion 250, and locking cap driver engagement portion 260 at another end of the shaft portion 250. In the illustrated embodiment, the reduction shaft engagement portion 255 may be configured and dimensioned to engage the reduction shaft 150. For example, the reduction shaft engagement portion 255 may be configured and dimensioned to engage a corresponding tool engagement surface (e.g., polygonal recess 220) of the connector portion 205 of the reduction shaft 150. In the illustrated embodiment, the reduction shaft engagement portion 255 is polygonal in shape for engaging the polygonal recess 220 of the reduction shaft 155. However, the present invention is intended to encompass a reduction shaft engagement portion 255 having other shapes, such as a slot or cross, that may be used, for example. In an alternative embodiment (not illustrated), the reduction shaft engagement portion 255 may be configured with a recess that may engage with the connector portion 205 of the reduction shaft 150 having a corresponding protrusion. The locking cap driver engagement portion 260 may have be configured and dimensioned to engage the locking cap driver 155. For example, the locking cap driver engagement portion 260 may be configured and dimensioned to engage a corresponding tool engagement surface (e.g., polygonal protrusion 245) of the driver connector portion 240 of the locking cap driver 155. In the illustrated embodiment, the locking cap driver engagement portion 260 includes a polygonal recess 265 for engaging the polygonal protrusion 245 of the locking cap driver 155. However, the present invention is intended to encompass locking cap driver engagement portion 260 having other shapes, such as a slot or cross, that may be used, for example. In an alternative embodiment (not illustrated), the locking cap driver engagement portion 260 may be configured with a protrusion that may engage with the driver connector portion 240 of the locking cap driver 155. In addition, the locking cap driver engagement portion 260 and/or the reduction shaft engagement portion 255 may each be configured and adapted to connect to a handle that may facilitate connection to a handle or other instrument.

Referring now to FIGS. 1-7, one embodiment for using the rod-reducing system 5 for reducing the rod 45 into the head 40 of the orthopedic fixation device 25 will be described. As illustrated by FIG. 1, the orthopedic fixation device 25 may be secured into the vertebral body 35 with the bone fastener 30 implanted into the vertebral body. Once secured, the housing 145 of the rod-reducing apparatus 15 may be coupled to tabs 115 of the reducing head 10. As previously mentioned, the tabs 115 extend from the head 40 of the orthopedic fixation device 25, as best seen in FIG. 5. To couple the housing 145 and the tabs 115, the extension 165 at the distal end of the housing 145 may be placed into the channel 130 between the tabs 115 and rotated to engage the extension 165 into the tabs 115, as best seen in FIG. 5. The rod-reducing apparatus should now be secured to the reducing head 10 with the locking cap assembly 25 retained by the locking cap driver 155, and the rod 45 positioned below the locking cap assembly 25, as best seen in FIG. 1. Next, the reduction shaft 150 can be driven with the driving apparatus 20. For example, the driving apparatus 20 may be rotated to thread the reduction shaft 150 through the housing 145, thus reducing the rod 45 into the head 40 of the orthopedic fixation device 24. Reduction of the rod 45 into the head 40 should also position the locking cap assembly 50 with the locking cap 235 (e.g., FIG. 5) in the head 40 of the orthopedic fixation device. Once the locking cap 235 aligns with the slots 105 in the upper portion of the head 40, the locking cap driver 155 can be manipulated to engage the locking cap 235 into the head 40. For example, the locking cap driver 155 can be rotated to rotate the locking cap 235 such that protrusions (not illustrated) on the locking cap 235 engage the slots 105 in the head 40. The locking cap 235, in some embodiments, should apply downward force onto the rod 45 holding it in place. With the locking cap 235 engaged with the head 40, the locking cap driver 155 can also be manipulated to thread the set screw 232 (e.g., FIG. 5) downward through the locking cap 235 to engage the rod 45. The set screw 232, for example, should apply additional downward pressure onto the rod 45 holding it in place. Next, the rod-reducing apparatus 15 can be disengaged from the reducing head 10. For example, the rod-reducing apparatus 15 can be rotated to disengage the extension from housing 145 from the tabs 115 of the reducing head 10. Because the reduction shaft 150 was threaded into the housing 145 and not the reducing head 10, the reducing apparatus 15 can be quickly removed without having to unthread the reduction shaft 150. Next, the reducing head 10 can be removed from the head 40 of the orthopedic fixation device 25. For example, the tabs 115 can be broken at connection point 125 (FIG. 2) to remove the reducing head 10 from the head 40.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims. Although individual embodiments are discussed herein, the invention covers all combinations of all those embodiments.

What is claimed is:
1. A rod-reducing apparatus:
a housing comprising a threaded through bore;
a reduction shaft comprising a shaft portion and a through bore in the shaft portion, wherein the shaft portion is configured to be received within the threaded through bore of the housing;
a locking cap driver comprising a shaft portion that is configured to be received within the through bore of the reduction shaft, wherein a distal end of the shaft portion of the locking cap driver is configured for attachment to a locking cap assembly,
wherein the housing comprises a clip-on assembly coupled to the housing to secure the housing to a reducing head,
wherein the clip-on assembly includes a pair of clip-on tabs, each having a proximal end and a distal end, and a spring disposed between the pair of tabs at the proximal end, and
wherein the housing comprises an extension configured to couple the rod-reducing apparatus to the reducing head, wherein the reducing head comprises tabs that define a channel for receiving the extension.

2. The rod-reducing apparatus of claim 1, wherein the spring is configured to bias the clip-on tabs to secure the housing to a reducing head.

3. The rod-reducing apparatus of claim 1, wherein a proximal end of the reduction shaft comprises a connector portion configured to engage a driving apparatus.

4. The rod-reducing apparatus of claim 3, wherein a proximal end of the locking cap driver comprises a driver connector portion configured to engage the driving apparatus.

5. The rod-reducing apparatus of claim 4, wherein the connector portion of the reduction shaft comprises a polygonal recess configured to engage a corresponding protrusion on the driving apparatus, and wherein the driver connector portion of the locking cap drive comprises a polygonal protrusion configured to engage a corresponding recess on the driving apparatus.

6. A rod-reducing system comprising:
a reducing head comprising tabs, wherein a channel is defined between the tabs;
a driving apparatus comprising a shaft portion;
a rod-reducing apparatus, wherein the rod-reducing apparatus comprises:
a housing comprising a threaded through bore, wherein the housing is configured for attachment to the tabs of the reducing head;
a reduction shaft comprising a shaft portion, a connector portion at a proximal end of the shaft portion of the reduction shaft, and a through bore in the shaft portion of the reduction shaft, wherein the shaft portion of the reduction shaft is configured to be received within the threaded through bore of the housing, wherein the connector portion is configured for engagement with the driving apparatus; and
a locking cap driver comprising a shaft portion that is configured to be received within the through bore of the reduction shaft, wherein a distal end of the shaft portion of the locking cap driver is configured for engagement with a locking cap assembly, and wherein a proximal end of the shaft portion of the locking cap driver is configured for engagement with the driving apparatus;
wherein the reduction shaft is configured to thread through the housing and into the channel in the reducing head with the shaft portion of the locking cap driver disposed in the through bore in the reduction shaft,
wherein the housing comprises a clip-on assembly coupled to the housing to secure the housing to the reducing head, and
wherein the clip-on assembly is configured to attach to an outer surface of the reducing head.

7. The rod-reducing system of claim 6, wherein the tabs are each extensions of a corresponding sidewall of the reducing head.

8. The rod-reducing system of claim 6, wherein the reducing head is part of an orthopedic fixation device further including a bone fastener configured to secure the orthopedic fixation device in bone, wherein the reducing head comprises a bottom portion having an opening for receiving a base portion of the bone fastener and sidewalls that extend from the bottom portion.

9. The rod-reducing system of claim 8, wherein the tabs and the sidewalls are coupled at an area of reduced diameter with respect to the tabs.

10. The rod-reducing system of claim 6, wherein the driving apparatus comprises a first end configured for engagement with the proximal end of the reduction shaft and a second end configured for engagement with the proximal end of the locking cap driver.

11. The rod-reducing system of claim 10, wherein the proximal end of the reduction shaft comprises a polygonal recess configured for engagement with the first end of the driving apparatus, wherein the proximal end of the locking cap driver comprises a polygonal protrusion configured for engagement with the second end of the driving apparatus.

12. The rod-reducing system apparatus of claim 6, wherein the clip-on assembly comprises protuberances configured to couple the rod-reducing apparatus to the reducing head.

13. The rod-reducing system of claim 12, wherein the protuberances are configured for engagement with a corresponding recess in the tabs of the reducing head.

14. The rod-reducing system of claim 6, wherein the clip-on assembly comprises clip-on tabs and a spring configured to bias the clip-on tabs to secure the housing to the reducing head.

\* \* \* \* \*